United States Patent [19]

Akimova et al.

[11] Patent Number: 4,981,483
[45] Date of Patent: Jan. 1, 1991

[54] BIOCOMPATIBLE MATERIAL FOR TREATMENT OF TISSULAR OR ORGANIC DEFECTS

[76] Inventors: Alla Y. Akimova, ulitsa Petrozavodskaya, 5, korpus 3, kv. 391; Anatoly B. Davydov, ulitsa Krasny Kazanets, 19, korpus 1, kv. 283; Valery N. Egiev, Volgogradsky prospekt, 71, korpus 1, kv. 156, all of Moscow; Anna I. Iliina, Moskovsky prospekt 3, kv. 17, Moskovskaya oblast Pushkino; Jury P. Kapustin, Chistoprudny bulvar, 12, korpus 2, kv. 18, Moscow; Anesty K. Orfanidi, ulitsa Festivalnaya, 59, korpus 1, kv. 11, Moscow; Alexei N. Smirnov, ulitsa Kuusinena, 7, kv. 64, Moscow; Eduard A. Stepanov, ulitsa Ostrovityanova, 30, korpus 2, kv. 37, Moscow; Valeria I. Timokhina, Yaroslavskoe shosse, 4, korpus 4, kv. 377, Moscow; Anatoly Nikolaevich Chigir, ulitsa Veernaya, 7, korpus 2, kv. 188, Moscow; Kirill G. Schitkov, ulitsa 15 Parkovaya, 46, korpus 4, kv. 41, Moscow, all of U.S.S.R.

[21] Appl. No.: 266,633
[22] PCT Filed: Jan. 14, 1987
[86] PCT No.: PCT/SU87/00002
§ 371 Date: Aug. 23, 1988
§ 102(e) Date: Aug. 23, 1988
[87] PCT Pub. No.: WO88/05311
PCT Pub. Date: Jul. 28, 1988
[51] Int. Cl.$^5$ ............................................. A61B 17/04
[52] U.S. Cl. ..................................... 606/214; 623/66
[58] Field of Search .................... 623/66, 16; 606/214, 606/215

[56] References Cited

U.S. PATENT DOCUMENTS

| | | |
|---|---|---|
| 3,630,194 | 12/1971 | Boardman . |
| 3,667,472 | 6/1972 | Halpern .............................. 606/214 |
| 3,759,264 | 9/1973 | Coover, Jr. et al. ................ 606/214 |
| 4,316,457 | 2/1982 | Liegeois . |
| 4,746,544 | 5/1988 | Hogen-Esch ...................... 427/140 |

FOREIGN PATENT DOCUMENTS

| | | |
|---|---|---|
| 899078 | 9/1984 | Belgium . |
| 1221282 | 2/1971 | United Kingdom . |

OTHER PUBLICATIONS

"Surgery" Meditsina Publishers 1982.

*Primary Examiner*—Alan W. Cannon
*Attorney, Agent, or Firm*—Burgess, Ryan & Wayne

[57] ABSTRACT

A biocompatible material for treatment of tissular or organic defects is composed of a graft copolymer of alpha-cyanacrylate and polyacrylic acid having a molecular weight of 200,000 to 600,000, obtained by interaction of alpha-cyanacrylate with polyacrylic acid in the presence of a cross-linking agent, the weight percentage ratio of the aforesaid components being as follows:

| | |
|---|---|
| alpha-cyanacrylate | 14 to 34 |
| polyacrylic acid having a molecular weight of 200,000 to 600,000 | 15 to 43 |
| cross-linking agent | 71 to 23 |

4 Claims, No Drawings

BIOCOMPATIBLE MATERIAL FOR TREATMENT OF TISSULAR OR ORGANIC DEFECTS

FIELD OF THE INVENTION

The present invention relates to medicine and has particular reference to a biocompatible material for treatment of tissular or organic defects.

PRIOR ART

Known in the present state of the art is a composition for connective elements of soft tissues and organs based on resorbable-polymers and comprising a copolymer of N-vinyl-pyrrolidone and alkyl acrylates and/or alkyl methacrylates which contain 2 to 8 carbon atoms in their alkyl group (BE,A, N 899078). The connective elements are in fact sheets and films of preset configuration and are employed mostly in reuniting and hermetically sealing incised or resected portions of the parenchymatous organs. The film is resorbed in the organism within 35 to 250 days, its tensile strength ranging within 6.7 and 18.8 kgf/cm$^2$ and percentage elongation after a 30-minute holding in physiological saline (which is a measure of its elasticity in a swollen state) varying from 21 to 880.

However, the compositions mentioned above are characterized by the fact that when in the form of dry films, they are brittle; therefore, the films should be placed in physiological saline within 10 to 15 minutes before use in order to impart adequate elasticity thereto.

On the other hand, higher elasticity of the films (characterized by their percentage elongation) results in a reduced strength of the material. Since the resorption period of the films exceeds the regeneration period of the soft tissues, the latter have no time enough to grow into the connective elements.

Besides since the material of the connective elements does not allow one to adjust its absorbability characterized by the degree of swelling, it cannot be used for treatment of suppurative skin lesions and operative wounds.

Known to be used commonly is also the material Debrisan (available from Pharmacea Co, Sweden) which is applicable for treatment of suppurative wounds (cf. the journal "Surgery", Meditsina Publishers, Moscow, No. 8, 1982, pp. 88-91 (in Russian). Debrisan appears as a white powder consisting of destran polymers; it features high degree of absorbability, i.e., 4 ml per gram of the agent. Debrisan is poured into the wound, then a moistened towelette is placed thereon and a piece of wax paper is put atop. Dressings are to be changed daily, the powder being removed by gauze balls and washed off with any suitable solution. Application of Debrisan contributes to debridement and drying of the wound and reduces the degree of edema. However, application of Debrisan is ineffective when the wound is invaded with blue pus bacillus, as well as in case of acute suppuration of the wound. In such a case administration of antibacterial drugs within the initial 2 or 3 days is more effective.

In addition, application of Debrisan to and its removal from deep wounds or fistular cavities is difficult.

DISCLOSURE OF THE INVENTION

It is an object of the present invention to provide a biocompatible material for treatment of tissular or organic defects that possess adjustable absorbability and resorption rate coordinated with tissue regeneration rate, and features higher elasticity in combination with adequately high strength.

The aforesaid object is accomplished due to the fact that a biocompatible material for treatment of tissular or organic defects based on a resorbable polymer, according to the invention, comprises a graft copolymer of alpha-cyanacrylate and polyacrylic acid having a molecular weight of 200,000 to 600,000 and obtained by the interreaction of alpha-cyanacrylate with polyacrylic acid in the presence of a cross-linking agent, the weight percentage ratio of the aforesaid components being as follows:

| | |
|---|---|
| alpha-cyanacrylate | 14 to 34 |
| Polyacrylic acid having a molecular weight of 200,000 to 600,000 | 15 to 43 |
| cross-linking agent | 71 to 23 |

The biocompatible material as herein claimed comprises as alpha-cyanacrylate preferably ethyl-alpha-cyanacrylate, ethoxy-ethyl-alpha-cyanacrylate, butyl-alpha-cyanacrylate, or mixtures thereof.

The biocompatible material herein claimed comprises as a cross-linking agent polyvinyl alcohol having a molecular weight of 50,000 to 60,000, glycerol, or a mixture thereof. The biocompatible material of the invention can be obtained in the form of dia. 0.5 to 1.5 mm granules, or dia. 0.8 to 2.5 mm strings, films 100 to 1000 $\mu$m thick, sheets 10 to 50 mm thick, sheets with a developed surface providing a maximum area of contact with the wound.

The density ($\rho$) of the material ranges from 0.16 to 0.8 g/cm$^3$, the absorbability characterized by the daily swelling weight percent increment (A) varying from 500 to 15000, percentage elongation (E) at tension characterizing elasticity, ranging from 10 to 150 percent, and ultimate tensile strength, from 40 to 55 kgf/cm$^2$. The material is amenable to fragmentation and biodegradation under the effect of the biological fluids of human organism.

The degree of swelling of the biocompatible material may amount to 10000 or 15000 percent, which renders the material promising for treatment of suppurative skin lesions and operative wounds.

Whenever necessary the biocompatible material may be doped with some medicinal substances, e.g., antiseptics, and hence it is applicable in surgery and traumatology for prevention or stopping of infection. According to the invention, the biocompatible material contains preferably an antiseptic in an amount of 9 to 50 weight percent.

BEST MODE OF CARRYING OUT THE INVENTION

The biocompatible material of the invention is featured by such a resorption time that provides for its permanent replacement by the regenerating organism's tissue. A biocompatible material can be established within the limits of the aforestated formulation, said material being featured by comparatively high strength and elasticity when both dry and swollen, which renders it easily mouldable on intricately shaped surfaces. The degree of swelling of the biocompatible material that characerizes its absorbability may amount to 15000 percent within a 24-hour period, which makes the material promising for treatment of suppurative skin lesions and operative wounds.

The biocompatible material resulting from formulations that goes beyond the limits specified above, fails to meet, as for its characteristics, the requirements imposed thereon. Thus, the material resulting from the reaction of aqueous solutions of polyacrylic acid and polyvinyl alcohol with alpha-cyanacrylate taken in an amount below 14 percent, is liable to undergo fragmentation and biodegradation as early as in six hours after preparation and cannot therefore be used for closure and treatment of soft-tissue and organic defects. The biocompatible material resulting from the use of alpha-cyanacrylates taken in an amount exceeding 34 percent, features the resorption period in the organism exceeding two months, thus precluding its permanent replacement by the regenerating tissue, and cannot therefore be applied for closure and treatment of soft-tissue and organic defects.

The biocompatible material being claimed has studied experimentally on 20 male rats of the Vistar strain, weighing 200 to 240 g. Experiments were conducted on the test animals under inhalation ether narcosis. Once a 1.2 to 2.0 cm long incision had been made in the skin of the anterior abdominal wall, the skin was separated by the blunt technique from the subjacent muscles, whereupon a film measuring 1.0 to 1.5 cm in length was placed in the thus-formed pocket. The experiment results have demonstrated that vast proliferation of the granulation tissue occurs round the film and between the muscular fibers of the adjacent muscle on the seventh day after the implantation, and the tissue becomes collagenated on the side of the implant. A tendency is observed for a connective-tissue capsule to form round the film, which capsule is finally established to the subjacent muscles, and somewhere to the skin.

The film biodestruction process which begins in step with the start of the connective-tissue capsule formation, is practically terminated on the twenty-first or twenty-third day after surgery.

Histologic examination reveals accretion of some individual elements of the capsule between the muscular fibres at the spots where the capsule adheres to the muscle. Implantation of the material is accompanied by the development of neither drastic dystrophic nor necrobiotic changes in the subjacent muscular tissue.

The biocompatible material of the invention has been tested experimentally for closure of the pancreas on 10 sexually mature rats weighing 200 to 250 g each. The experiment was carried out with the test animals under inhalation ether narcosis. The supramedian laparotomy was made, the duodenum was brought through the operative wound together with the stomach, pancreas and spleen. A film measuring $2 \times 3$ cm$^2$ was placed on the pancreas, whereupon the gland was reinvaginated in the abdominal cavity and the operative wound was stitched up in layers. The test rats were withdrawn from the experiment within various periods after the surgery for being subjected to macroscopic and histologic examinations. In three weeks after surgery the film was found to be no longer in the abdominal cavity. Macroscopically the pancreas developed no perceptible change, no adhesions being observed in the abdominal cavity. Histologic examination demonstrated the normal structure of the organ without any symptoms of inflammatory alterations.

There has been studied also a possibility of application of the present biocompatible material reinforced with lavsan netting to restore the lost colic sphincter in children developing neurogenic disturbances of the pelvic organs. The experiment was carried out on 10 test cats using the following procedure. The distal segment of the rectum was exposed and embraced with a strip of the biocompatible material which was then stitched to the pubic bones. Thus, the rectum was drawn forward to establish the rectal sphincter. Morphologic examinations at terms from one to three months after surgery has shown that the biocompatible material is replaced by the cicatricial connective tissue which will subsequently serve as the sphincter of the rectum. Such a surgical procedure has been applied clinically in eight patients with complete rectal incontinence, a positive result being obtained in every case.

The present biocompatible material featuring high absorbability (the daily swelling percent ranging within 5000 and 15000) has been tested on liquid media to show that there occurs uniform absorbing of the microorganisms situated throughout the entire thickness of the material. The evidence obtained served as the grounds for application of the biocompatible material clinically for drainage of suppurative flat skin lesions in patients.

With such purpose in view the present biocompatible material has been used, comprising antiseptics, e.g., chlorophyllitum (an extract of eucalyptus leaves, containing a mixture of chlorophylls). The biocompatible material containing antiseptics has been applied to 15 patients clinically. In every case a markedly pronounced positive clinical effect has been observed, i.e., rapid depuration of the wound from purulent debris, change in the microbial count, quick appearance of granulations and marginal epithelialization, reduced healing period of the wound as compared with traditional treatment methods.

Plastic reparation of extensive defects of the anterior abdominal wall using the present biocompatible material in the form of sheets reinforced with lavsan netting has been studied experimentally on 50 test rats aged 2 to 2.5 months and weighing 150 g each. Four kinds of defects of the anterior abdominal wall were established by excisions arranged longitudinally and transversely and occupying 20 and 40 percent of the total abdominal wall area. Then the defect was covered with an oval piece of the reinforced biocompatible material, and the skin above it was stitched up. The results of the experiment have demonstrated the healing of the operative skin wound to occur by first intention. Morphologic examination of excised preparations of the anterior abdominal wall of the test rats carried out one, two, and three months after surgery has demonstrated good replacement of the present biocompatible material by connective tissue without any symptoms of an inflammatory process. On the part of the abdominal cavity, there were exhibited no manifestations of adhesion of the intestinal loops to the anterior abdominal wall, the inner surface of the repaired defect had a peritoneum-like lining provided with a developed network of small vessels. Similar surgical procedure was carried out clinically in 6 patients suffering from embryonal hernias and gastroschisis. In all cases the defect of the anterior abdominal wall was managed to be closed completely, while the operating time was cut down considerably.

The biocompatible material consisting of a graft copolymer of alpha-cyanacrylate with polyacrylic acid, is prepared by mixing a solution of alpha-cyanacrylate in an organic solvent that does not polymerize alpha-cyanacrylate and is immiscible with water, with an aqueous solution of polyacrylic acid having a molecular weight of 200,000 to 600,000, and a cross-linking agent, preferably polyvinyl alcohol having a molecular weight of 50,000 to 60,000, or glycerol, or a mixture of both, until an emulsion is obtained. The biocompatible material in the form of films or sheets is obtained by casting the emulsion, in the form of granules, by pouring the emulsion dropwise into a settling bath (an electrolyte solution), and in the form of strings, by extruding through a profiled die or spinneret into a settling bath. The solvents are then removed by one of the known methods, e.g., by holding the finished product within a definite temperature interval. After having been dried the finished product from the biocompatible material in the form of films, sheets, granules, or strings may be additionally subjected to heat treatment to produce cross-linked polymers.

Characteristic curves of the differential-thermal analysis of the films produced by the aforresaid method, confirm the presence of an interaction between alpha-cyanacrylates and polyacrylic acid, thus differing from the characteristic curves obtained with homopolymers (such as polyethylalpha-cyanacrylate, polyacrylic acid, and mechanical mixtures of both). The nitrogen content of the specimens of the biocompatible material being claimed ranges within 1.10 and 3.84 weight percent.

For a better understanding of the present invention, the following examples of the biocompatible material as therein claimed are given below by way of illustration.

EXAMPLE 1

The biocompatible material, comprising a graft copolymer of alpha-cyanacrylate and polyacrylic acid having a molecular weight of 200,000 to 600,000, is prepared by the interaction of alpha-cyanacrylate with polyacrylic acid in the presence of a cross-linking agent, viz., a mixture of polyvinyl alcohol having a molecular weight of 50,000 to 60,000, with glycerol, the weight percentage ratio of the aforesaid components being as follows:

| | |
|---|---|
| mixture of ethyl-alpha-cyanacrylate and ethoxyethyl-alpha-cyanacrylate (1:1) | 19 |
| polyacrylic acid having a molecular weight of 200,000 to 600,000 | 35 |
| polyvinyl alcohol having a molecular weight of 50,000 to 60,000 | 35 |
| glycerol | 11 |

The aforementioned material is prepared by mixing a solution of 0.790 g (19 weight percent) of ethyl-alpha-cyanacrylate and ethoxyethyl-alpha-cyanacrylate taken in a ratio of 1:1, in chloroform, and an aqueous solution of 1.41 g (35 weight percent) of polyacrylic acid having a molecular weight of 200,000 to 600,000 in the presence of 1.41 (35 weight percent) of polyvinyl alcohol having a molecular weight of 50,000 to 60,000 and 0.46 g (11 weight percent) of glycerol.

Then a film is formed by the casting method with the use of an extrusion die or spinneret, whereupon the solvent is eliminated at 37° to 39° C. Next the thus-obtained film is subjected to heat treatment at 100° C. within 60 min. The biocompatible material which is in effect a cross-linked graft copolymer of alpha-cyanacrylate and polyacrylic acid, is prepared as a foamed film having the following characteristics:

| | |
|---|---|
| thickness | 400 μm |
| absorbability (in terms of daily swelling percentage) | 1250 |
| percentage elongation at tension | 125 |
| density | 0.36 g/cm$^3$ |
| ultimate tensile strength | 54 kgf/cm$^2$ |

EXAMPLE 2

The biocompatible material, comprising a graft copolymer of ethyl-alpha-cyanacrylate and polyacrylic acid having a molecular weight of 200,000 to 600,000 is prepared by interaction of ethyl-alpha-cyanacrylate with polyacrylic acid in the presence of a mixture of polyvinyl alcohol and glycerol, the weight percentage ratio of the aforesaid original components being as follows:

| | |
|---|---|
| ethyl-alpha-cyanacrylate | 34 |
| polyacrylic acid having a molecular weight of 200,000 to 600,000 | 43 |
| polyvinyl alcohol having a molecular weight of 50,000 to 60,000 | 21 |
| glycerol | 2 |

The aforesaid material is prepared by reacting a solution of 3.25 g (34 weight percent) of ethyl-alpha-cyanacrylate in benzene and an aqueous solution of 4.1 g (43 weight percent) of polyacrylic acid having the aforesaid molecular weight, in the presence of 2.0 g (21 weight percent) of polyvinyl alcohol and 0.19 g (2 weight percent) of glycerol. The resultant emulsion is poured onto a back-up plate that provides for formation of a sheet with developed surface. Then the back-up plate along with the material in question is placed in a bath containing an aqueous sodium chloride solution and kept there for two hours. The biocompatible material obtained after drying and heat treatment is in fact a cross-linked graft copolymer of ethyl-alpha-cyanacrylate with polyacrylic acid and appears as a sheet having developed surface and featured by the following characteristics:

| | |
|---|---|
| thickness | 30 to 50 mm |
| absorbability (in terms of daily swelling percentage) | 500 |
| density | 0.17 g/cm$^2$ |

EXAMPLE 3

The biocompatible material composed of a graft copolymer of butyl-alpha-cyanacrylate and polyacrylic acid having a molecular weight of 200,000 to 600,000, is prepared by interaction of butyl-alpha-cyanacrylate with polyacrylic acid in the presence of polyvinyl alcohol, the weight percentage ratio of the aforementioned components being as follows:

| | |
|---|---|
| butyl-alpha-cyanacrylate | 24 |
| polyacrylic acid having a molecular weight of 200,000 to 600,000 | 38 |
| polyvinyl alcohol having a molecular weight of 50,000 to 60,000 | 38 |

The aforesaid material is prepared by interaction of a solution of 1.1 g (24 weight percent) of butyl-alpha-cyanacrylate in dibutyl ether with an aqueous solution of 1.7 g (38 weight percent) of polyacrylic acid having the aforesaid molecular weight, in the presence of 1.7 g (38 weight percent) of polyvinyl alcohol having a molecular weight of 50,000 to 60,000. The thus-obtained emulsion is poured, while stirring, dropwise into a settling bath, containing a sodium chloride solution. In three hours after completing the pouring of the emulsion the resultant granules are filtered out and dried by any of the heretoforeknown methods.

The biocompatible material appearing as granules is in fact a graft copolymer of butyl-alpha-cyanacrylate and polyacrylic acid cross-linked with polyvinyl alcohol and features the following characteristics:

| average granule diameter | 1 to 2 mm |
| absorbability (in terms of daily swelling percentage) | 15000 |
| density | 0.4 g/cm$^3$ |

EXAMPLE 4

The biocompatible material, composed of a graft copolymer of ethoxyethyl-alpha-cyanacrylate and polyacrylic acid is obtained by interaction of ethoxyethyl-alpha-cyanacrylate with polyacrylic acid in the presence of a mixture of polyvinyl alcohol with glycerol, the weight percentage ratio of the aforesaid components being as follows:

| ethyl-alpha-cyanacrylate | 14 |
| polyacrylic acid having a molecular weight of 200,000 to 600,000 | 15 |
| polyvinyl alcohol having a molecular weight of 50,000 to 60,000 | 60 |
| glycerol | 11 |

The aforesaid material is prepared by interaction of a solution of 1.3 g (14 weight percent) of ethoxyethyl-alpha-cyanacrylate an aqueous solution of 1.4 g (15 weight percent) of polyacrylic acid having a molecular weight of 200,000 to 600,000 in the presence of 5.6 g (60 weight percent) of polyvinyl alcohol having a molecular weight of 50,000 to 60,000 and 1.0 g (11 weight percent) of glycerol. One half of the thus-obtained emulsion (by volume) is applied, through an extrusion die or spinneret, to a backing-up plate, then a polyethyleneterephthalate (lavsan) net of a required size is placed on the spread layer of the emulsion, and the other half (by volume) of the emulsion is applied thereto. Then the solvents are removed at 37° to 40° C., and the material is subjected to heat treatment at 90° C. for 90 min.

The biocompatible material appearing as a sheet reinforced with lavsan netting is in fact a graft copolymer of ethoxyethyl-alpha-cyanacrylate and polyacrylic acid cross-linked with polyvinyl alcohol and glycerol, its characteristics being as follows:

| thickness | 1.2 mm |
| density | 0.23 g/cm$^3$ |
| absorbility (in terms daily swelling percentage) | 600 |
| resorption period of polymeric matrix in muscular tissue | 30 to 40 days |

EXAMPLE 5

The biocompatible material, composed of a graft copolymer of alpha-cyanacrylate and polyacrylic acid is obtained by interaction of a mixture of ethyl-alpha-cyanacrylate and ethoxyethyl-alpha-cyanacrylate (1:1) with polyacrylic acid in the presence of glycerol and an antiseptic, viz., chlorhexidine gluconate (1,6-di(N-p-chlorophenyldiguanido) hexane digluconate), the weight percentage ratio of the aforesaid components being as follows:

| mixture of ethyl-alpha-cyanacrylate and ethoxyethyl-alpha-cyanacrylate | 30 |
| polyacrylic acid having a molecular weight of 200,000 to 600,000 | 43 |
| glycerol | 27 |
| chlorhexidine gluconate | 9(of a total weight of the above components) |

The aforesaid material is prepared by interaction of a solution of 3.3 g (30 weight percent) of ethyl-alpha-cyanacrylate and ethoxyethyl-alpha-cyanacrylate in a ratio of 1:1, in hexane with an aqueous solution of 4.7 g (43 weight percent) of polyacrylic acid having a molecular weight of 200,000 to 600,000 in the presence of 3.0 g (27 weight percent) of glycerol and 0.99 g chlorhexidine gluconate (9 percent of a total weight of the aforesaid components). Then the resultant composition is extruded through a profiled die or spinneret into a settling bath containing a sodium chloride solution to shape the material as strings. Next the solvents are removed at 37° to 40°.

The biocompatible material which is in fact a graft copolymer of alpha-cyanacrylate and polyacrylic acid, containing an antiseptic, i.e., chlorhexidine gluconate, has the following characteristics:

| absorbability (in terms of daily swelling percentage) | 700 |
| antimicrobial activity against the strains of *staphylococci, colibacillus,* and other gram-positive bacteria | |

EXAMPLE 6

The biocompatible material, composed of a graft copolymer of alpha-cyanacrylate and polyacrylic acid having a molecular weight of 200,000 to 600,000 is obtained by interaction of a mixture of ethyl-alpha-cyanacrylate and ethoxyethyl-alpha-cyanacrylate (1:1) with polyacrylic acid in the presence of polyvinyl alcohol and an antiseptic, viz., gentamycin, the weight percentage ratio of the original components being as follows:

| mixture of ethyl-alpha-cyanacrylate and ethoxyethyl-alpha-cyanacrylate | 26 |
| polyacrylic acid having a molecular, weight of 200,000 to 600,000 | 37 |
| polyvinyl alcohol having molecular weight of 500,000 to 60,000 | 37 |
| gentamycin | 24 (of a total weight of the above components) |

The aforesaid material is obtained by interaction of a solution of 1.8 g (26 weight percent) of ethyl-alpha-cyanacrylate and ethoxyethyl-alpha-cyanacrylate taken in a ratio of 1:1, with an aqueous solution of 2.6 g (37 weight percent) of polyacrylic acid having a molecular weight of 200,000 to 600,000 in the presence of 2.6 g (37 weight percent) of polyvinyl alcohol having a molecular weight of 50,000 to 60,000 and 1.7 g gentamycin (24 percent of a total weight of the aforesaid components).

Then a film is formed by the casting method with the use of an extrusion die or spinneret, the solvents are removed at 37° to 40° C., the material is heat-treated at 100° C. for 60 min.

The biocompatible material which is in effect a graft copolymer of alpha-cyanacrylate and polyacrylic acid containing an antibiotic gentamycin, its characteristics being as follows:

absorbability (in terms of daily swelling percentage 150 antimicrobial activity against many gram-positive and gram-negative bacteria (colibacillus and staphylococci inclusive)

Industrial Applicability

The material of the invention can be applied for covering the pancreas both in normal state and in case of pancreatitis, for closing up the resected surface of the parenchymatous organs, for reparation of the dural defects, or of extensive defects of the anterior abdominal wall, for reparative surgery of the rectal sphincter, as well as for treatment of suppurative skin lesions and operative wounds.

What we claim is:

1. A biocompatible material for treatment of tissular or organic defects in a patient, said material comprised of a graft copolymer of alpha-cyanacrylate and polyacrylic acid having a molecular weight of 200,000 to 600,000, obtained by interaction of alpha-cyanoacrylate with polyacrylic acid in the presence of a cross-linking agent, the weight percentage ratio of the aforesaid components being as follows:

| | |
|---|---|
| alpha-cyanoacrylate | 14 to 34 |
| polyacrylic acid having a molecular weight of 200,000 to 600,000 | 15 to 43 |
| cross-linking agent | 71 to 23 | and wherein said material is resorbable by said patient.

2. A biocompatible material as claimed in claim 1, which comprises, as said alpha-cyanoacrylate, ethyl-alpha-cyanoacrylate, ethoxyethyl-alpha-cyanoacrylate, butyl-alpha-cyanoacrylate, or mixtures thereof.

3. A biocompatible material as claimed in claims 1 or 2, wherein said cross-linking agent is polyvinyl alcohol having a molecular weight of 500,000 to 600,000, glycerol or a mixture of both.

4. A biocompatible material as claimed in claims 1 or 2, which comprises additionally an antiseptic in an amount of 9 to 50 weight percent.

* * * * *